(12) United States Patent
Gelaude et al.

(10) Patent No.: US 9,289,221 B2
(45) Date of Patent: Mar. 22, 2016

(54) SHOULDER GUIDES

(71) Applicant: Materialise N.V., Leuven (BE)

(72) Inventors: Frederik Gelaude, Herent (BE); Koen Eraly, Kessel-Lo (BE)

(73) Assignee: Materialise N.V., Leuven (BE)

( * ) Notice: Subject to any disclaimer, the term of this patent is extended or adjusted under 35 U.S.C. 154(b) by 0 days.

(21) Appl. No.: 14/263,921

(22) Filed: Apr. 28, 2014

(65) Prior Publication Data

US 2014/0236158 A1   Aug. 21, 2014

Related U.S. Application Data

(63) Continuation of application No. PCT/EP2012/071272, filed on Oct. 26, 2012.

(60) Provisional application No. 61/552,543, filed on Oct. 28, 2011.

(51) Int. Cl.
| | |
|---|---|
| *A61F 5/00* | (2006.01) |
| *A61B 17/17* | (2006.01) |
| *A61B 17/56* | (2006.01) |
| *A61B 19/00* | (2006.01) |
| *A61B 17/00* | (2006.01) |

(52) U.S. Cl.
CPC ... *A61B 17/1739* (2013.01); *A61B 2017/00526* (2013.01); *A61B 2017/1778* (2013.01); *A61B 2017/568* (2013.01); *A61B 2019/508* (2013.01); *Y10T 29/49* (2015.01)

(58) Field of Classification Search
CPC combination set(s) only.
See application file for complete search history.

(56) References Cited

U.S. PATENT DOCUMENTS

| | | | |
|---|---|---|---|
| 2011/0029088 A1* | 2/2011 | Rauscher | A61B 17/1739 623/19.11 |
| 2011/0130795 A1 | 6/2011 | Ball | |

FOREIGN PATENT DOCUMENTS

| | | |
|---|---|---|
| EP | 2168507 A2 | 3/2010 |
| WO | 2011060536 A1 | 5/2011 |
| WO | 2011110374 A1 | 9/2011 |

OTHER PUBLICATIONS

International Search Report issued on related application PCT/EP2012/071272 dated Feb. 27, 2013.

* cited by examiner

*Primary Examiner* — Sameh Boles (57) ABSTRACT

The application provides patient-specific surgical guides for positioning onto a glenoid of a patient, comprising two or more patient-specific positioning elements, each comprising a patient-specific surface which conforms with at least part of one or more features of the bone on or around the glenoid, and wherein the combination of these patient-specific positioning elements ensures a secure fit of the device when positioned onto the bone.

12 Claims, 6 Drawing Sheets

SHOULDER GUIDES

CROSS-REFERENCE TO RELATED APPLICATIONS

This application is a continuation under 35 U.S.C. §120 of International Application No. PCT/EP2012/071272, filed Oct. 26, 2012 (published by the International Bureau as International Publication No. WO/2013/060851 on May 2, 2013), which claims priority to U.S. Provisional Patent Application No. 61/552,543, filed Oct. 28, 2011. The entire contents of each of the above-referenced applications are hereby incorporated by reference.

BACKGROUND OF THE INVENTION

1. Field of the Invention

Provided herein are patient-specific surgical devices that provide a stable fitted position for use in shoulder surgery, fitting within a typical surgical incision. The patient-specific surgical devices may be used for various purposes including for use as or with a shoulder guide.

2. Description of the Related Technology

Conventional orthopedic prostheses, guides and implants have been in use for many years with considerable success. The use of custom designed prostheses, guides and implant components based on the patient-specific anatomy has moreover overcome many shortcomings of the older designs. Such patient-specific devices can be developed using commercially available software. Typically such devices are used for orthopedic interventions to the spine, hip, knee and/or radius. Patient-specific devices available on the market include patient-specific knee replacement prostheses, patient-specific femoral and tibia cutting blocks, distal radius drilling, cutting templates, etc. At present, there exists an increasing amount of surgical interventions that benefit from the use of these medical image based patient specific surgical devices as described in patent applications US 2005/0203528 A1 and EP 1486900 A1, for instance.

While patient-specific devices such as guides are now typically used to accurately place pins, guide bone cuts or insert implants during orthopedic procedures, the correct positioning of these patient-specific devices remains a critical factor with important impact on the outcome of the procedure.

During surgical procedures on the shoulder, patient-specific devices such as guides are often used to position and guide surgical instruments such as pins, wires and drills which can be used for instance for guiding the initial pin placement during shoulder replacements.

Prior art devices are typically positioned on a limited number of anatomical sites with low inter-person variation, allowing the device to be standardized making the same device design available for a large number of patients. However, standardized surgical instruments typically provide the user with a reduced accuracy, leading to small deviation from the operative planning resulting in more complex surgery, or unexpected problems occurring during the surgical procedure. Here the use of customized instruments based on the exact anatomy of the patient would provide a large number of benefits as the inter-persons variation is not an issue for patient-specific instruments. However, when providing patient-specific instruments, for instance for patient-specific devices such as guides used during shoulder surgery, it is often seen that these patient-specific devices provide only a limited patient-specificity wherein the device still needs to be positioned manually by the surgeon, with limited visual aids.

Accordingly, there remains a need for improved patient-specific devices for performing shoulder surgery.

SUMMARY

Provided herein are patient-specific surgical devices that provide a stable fitted position for use in shoulder surgery, fitting within a typical surgical incision. The patient-specific surgical device may be used for various purposes including for use as or with a shoulder guide.

Typically the features of the devices envisaged herein restrict the movement of the device in both translational and rotational directions and thereby additionally provide the ability for the device to be uniquely positioned onto the glenoid in a repeatable way. This is ensured in different ways in the different embodiments described herein. Typically the guides as envisaged herein comprise one or more positioning elements linked to or forming an integral part of the guide body or support structure which allow a stable fitting on and/or around the glenoid.

Thus, provided herein are patient-specific devices such as surgical guides for positioning onto a glenoid of a patient, comprising a support structure, a guiding element; and two or more patient-specific positioning elements linked to or forming an integral part of the support structure, whereby each of the positioning elements may comprise a patient-specific surface which conforms with at least part of one or more features of the bone on or around the glenoid of said patient, and wherein the combination of said two or more patient-specific positioning elements ensures a secure fit of said device when positioned onto the bone.

In particular embodiments, one or more of the positioning elements ensures a clamping of the guide over at least part of the glenoid rim. An analysis of the glenoid revealed surface combinations which provide the optimal stability given the surgical incision or the available surgical exposure.

The patient-specific surgical devices as envisaged herein can be based on accurate medical image planning, thereby determining very accurately the entry point and the best axis direction, something which is not available for prior art devices.

In particular embodiments, the patient-specific surgical devices as envisaged herein are further provided with a patient-specific visual aid which matches exactly with the glenoid contour of the patient. Typical prior art instruments can be provided with a generic glenoid contour as visual aid, but again this is not a very accurate and helpful aid. The visual aid is typically used for the evaluation of the correct unique position of the guide after placement.

In particular embodiments, the devices as envisaged herein may comprise:

a support structure, optionally including a handle bar, a guiding element such as a drill cylinder or another feature for inserting and/or guiding a surgical tools such as a pin, a wire of a drill, and one or more positioning elements which are typically patient-specific elements in that they are designed to specifically interact with features on or around the glenoid of the patient. In particular embodiments these elements are selected from features including an anterior glenoid neck support, an inferior coracoid base support and support at the anterior and posterior glenoid surface and/or rim, and optionally a floating contour above the glenoid surface conform the glenoid rim geometry.

Also provided herein are methods for the development and manufacture of the surgical tools described herein. In particular embodiments, methods are envisaged for providing a patient-specific surgical guide for positioning onto a glenoid of a patient, which may comprise:

a) identifying and selecting, based on volume information of the glenoid from a patient, features of the bone on or surrounding the glenoid which are suitable for fitting patient-specific positioning elements; and b) designing, based on the installation direction of said surgical device and the information obtained in step a) a surgical device, comprising:
- a support structure;
- a guiding element; and
- two or more patient-specific positioning elements linked to or forming an integral part of said support structure, each comprising a patient-specific surface which conforms with at least part of one or more of said features of the bone on or around said glenoid, such that the combination of said two or more patient-specific positioning elements ensures a secure fit of said device when positioned onto the bone.

Further embodiments envisaged are described herein below.

BRIEF DESCRIPTION OF THE DRAWINGS

The following description of the figures of specific embodiments is merely exemplary in nature and is not intended to limit the present teachings, their application or uses. Throughout the drawings, corresponding reference numerals indicate like or corresponding parts and features.

1—patient-specific surgical guiding instrument; 2—support structure; 3—handle bar; 4—drill cylinder; 5—anterior glenoid neck support; 6—inferior coracoid base support; 7—support at the anterior and posterior glenoid surface and/or rim; 8—floating contour above the glenoid surface conform the glenoid rim geometry; 9—support at the coracoid tip; 10—locking feature, 11—hinge feature; 12—positioning element for clamping over the shoulder bone; 13—shoulder bone

DETAILED DESCRIPTION OF CERTAIN INVENTIVE EMBODIMENTS

The concepts provided herein are described with respect to particular embodiments but are not limited thereto but only by the claims. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited members, elements or method steps also include embodiments which "consist of" said recited members, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments described herein are capable of operation in other sequences than described or illustrated herein.

The term "about" as used herein when referring to a measurable value such as a parameter, an amount, a temporal duration, and the like, is meant to encompass variations of +/−10% or less, preferably +1-5% or less, more preferably +/−1% or less, and still more preferably +/−0.1% or less of and from the specified value, insofar such variations are appropriate to perform the same function. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in the present description, including technical and scientific terms, have the meaning as commonly understood by one of ordinary skill in the art. By means of further guidance, definitions for the terms used in the description are included to better appreciate the teaching of the concepts provided herein. The terms or definitions used herein are provided solely to aid in the understanding thereof.

Reference throughout this specification to "one embodiment" or "an embodiment" means that a particular feature, structure or characteristic described in connection with the embodiment is included in at least one embodiment as envisaged herein. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of teachings provided herein, and form different embodiments, as would be understood by those in the art. For example, in the following any of the described embodiments can be used in any combination.

Provided herein are patient-specific surgical devices that provide a stable fitted position for use in shoulder surgery, fitting within a typical surgical incision. The patient-specific surgical devices may be used for various purposes including for use as or with a shoulder guide.

More particularly, the patient-specific surgical devices envisaged herein are shoulder guides for guiding or positioning surgical instruments such as guides, wires and/or drills for use during shoulder surgery, and more particularly for the initial pin placement during shoulder replacements.

It has been found that surgical devices for positioning on the glenoid can be provided with an optimal stability and a high accuracy by using specific anatomical structures supports, thereby providing much more stable devices which are more easily positioned in their accurate position. With this aim, patient-specific instruments are provided, which are characterized by the presence of patient-specific positioning elements which are complementary with anatomical features. These provide the guide with the required accuracy and stability. When selecting these features it should of course be ensured that the chosen anatomical locations are reachable during surgery as a support location.

The surgical devices such as guides envisaged herein are designed to ensure a restriction of movement of the device in both translational and rotational directions of the guide after placement on the glenoid. In addition, by the provision of patient-specific positioning elements, they make it easier for the guide to be uniquely positioned onto the glenoid in a repeatable way. The patient-specific surgical devices envisaged herein can be based on accurate medical image planning, thereby determining very accurately the entry point and the best axis direction, something which is not available for prior art devices.

As used herein, the term "patient-specific device" relates to any surgical, therapeutic or diagnostic devices or tools such as an implant, a prosthesis or a guide which is designed based on an individual patient's anatomy to include features which have a custom fit or perform a customized function for a specific location in a specific patient. The use of patient-specific guides and implants allows to ensure an improved or optimized accuracy of the surgical intervention and an improved anatomical fit for prosthetic structures so as to ensure optimized functionality for each patient. Even when such devices are used in combination with standard implants, tools, devices, surgical procedures, and/or other methods important benefits in accuracy of placement can be obtained. Accordingly, the term "patient-specific device" is used to refer to a custom-made device specific to the individual patient's anatomy. More particularly, the device is a device comprising at least one surface which conforms or is complementary with at least part of the patient's anatomy.

The terms "surgical guiding tool" and "guiding tool" as used herein refer to (patient-specific) surgical tools that can be positioned onto an anatomical part of a patient and that help a surgeon in the accurate positioning of an alignment element and/or guidance of other surgical instruments, such as drilling or cutting tools. Thus, guiding tools typically may comprise a "guiding element" which is a dedicated feature for guiding a positioning tool or cutting or drilling elements. Examples of guiding elements are detailed herein below.

The term "glenoid implant and/or guide" as used herein refers to a component of a prosthetic shoulder implant or guide which is placed into or onto the glenoid cavity of a patient. Such implants or guides may be used in a (total) shoulder arthroplasty or reverse (total) shoulder arthroplasty. The glenoid cavity, also known as glenoid fossa (of the scapula), is a shallow surface, which is located on the lateral angle of the scapula. This cavity forms the glenohumeral joint along with the humerus. The part of the bone encompassing the glenoid cavity including the glenoid rim is also referred to herein as "the glenoid".

Typically the surgical devices such as guiding tools as envisaged herein comprise a guide body or support structure and one or more positioning elements linked to or forming an integral part of the guide body or support structure which allow a stable fitting on the glenoid or part thereof. The "positioning elements" of the devices envisaged herein ensure positioning of the device onto a specific area of the bone. More particularly the devices provided herein comprise at least two positioning elements which each contact a discrete area of the bone. In particular embodiments, the positioning elements of the devices envisaged herein are characterized in that they each comprise a patient-specific surface which conforms with at least part of a features of the glenoid. These are referred to as patient-specific positioning elements. It is further envisaged herein that the devices comprise two or more positioning elements which are selected such that the combination of said two or more positioning elements ensures a secure fit of said device when positioned onto the bone.

In particular embodiments, the positioning elements ensure a clamping of the guide over at least part of the glenoid rim. The one or more positioning elements may be reversibly connected to or form an integral part of the body of the surgical guide. It will be understood to the skilled person hat in the devices envisaged herein, the different positioning elements are at least (reversibly) interconnected through the support structure. Moreover, in particular embodiments, the positioning elements may be irreversibly joined together.

The surgical guides envisaged herein are guides comprising at least one surface which conforms or is complementary with at least part of the patient's anatomy. This surface may be present on the body of the device and may also be part of the positioning elements as indicated above. The complementary surface is also referred herein as a "patient-specific element".

An analysis of the glenoid may reveal surface combinations which provide the optimal stability given the surgical incision or the available surgical exposure.

The patient-specific surgical devices as envisaged herein specifically comprise patient-specific elements (i.e. contact surfaces) and/or positioning elements interacting with or at least partially complementary with specific features of the glenoid, or specific features around the glenoid, i.e. the anatomy surrounding the glenoid. Exemplary features include, but are not limited to the (base or tip of the) coracoid process, the (anterior or posterior) glenoid neck, the glenoid surface, and the glenoid rim. Interaction of the device with one or more of these features, optimally based on patient-specific information thereof, allows for a structure which not only fits particularly well onto the bone of the patient, but which may also limit the movement of the device when accurately placed thereon. Indeed, in particular embodiments, the features are selected such that the interaction with a combination thereof imposes a restriction on the movement of the device when placed thereon. More particularly the features are selected such that the patient-specific elements and/or positioning elements restrict movement of the device in both translational and rotational directions.

In particular embodiments the devices comprise one or more patient-specific elements and/or positioning elements which interact or are complementary to at least two or more, more particularly all three of features of the glenoid recited above. Typically, this is combined with patient-specific elements or positioning elements interacting with or complementary to other parts of the shoulder bone. The patient-specific elements and positioning elements can be separate elements interacting with different features or one patient-specific element can interact with different features by extending over the different features.

The patient-specific devices such as surgical guides envisaged herein thus comprise patient-specific elements such as contact surfaces and (patient-specific) positioning elements, which fit onto areas on and/or around specific anatomical features of the glenoid. Starting from the fully exposed anatomy and a given position for the functional feature, the surrounding anatomy of the glenoid can be analyzed, thereby determining the surface combinations providing the optimal stability for the patient-specific device. The analysis of the stability provides the measures for the translational and rotational stability of the patient-specific guide.

In particular embodiments, the structure of the positioning element helps to ensure stable positioning of the device on the bone. For instance, in particular embodiments, at least one positioning element may comprise a hinge. In certain embodiments, this may facilitate clamping the positioning element onto the anatomy of the shoulder bone, so as to ensure a tight fit of the surgical device over the bone. In particular embodiments, the device may comprise two positioning elements which interact with opposing sides of the contour of the glenoid, such that the device can be tightly locked around the glenoid. The presence of a hinge on one or both of the positioning elements facilitates positioning and removal of the device. In particular embodiments, one or more positioning elements may interact with specific features round the glenoid, such as the coracoid process. Such a positioning element having a patient-specific surface may further ensure the correct positioning of the device.

The devices and methods provided herein can be applied to the field of implant and/or guide surgery, more particularly implants and/or which are placed into a socket of a ball-and-socket joint, and typically the glenoid. For human patients, this is a glenoid implant and/or a glenoid guide.

The devices such as the patient-specific surgical guides envisaged herein typically comprise one or more dedicated functional features, the functional features may be required during the surgical procedure. The functional features may be integrated in the remainder of the device but may also be removably connected thereto. These functional features include, but are not limited to a wire, pin, screw or drill, particularly a metal wire, pin, screw or drill.

Where the devices envisaged herein are guiding tools, they will comprise as functional features one or more guiding elements, which may be integrated in the remainder of the device but may also be removably connected thereto. In particular embodiments, the device is a patient-specific surgical guide and may comprise a functional feature which is a guiding feature for a surgical instrument or tool such as, but not limited to a slot or a cylinder.

In particular embodiments, the device such as a patient-specific surgical guide may comprise a functional feature which is an alignment element or a feature suitable for interaction with an alignment element. In particular embodiments, the alignment element is a wire or a pin, particularly a Kirschner wire (K-wire), a Hoffmann pin or a drilling pin.

The functional features interacting with a surgical instrument or tool according to specific embodiments envisaged herein may include, but are not limited to guides or holes for interacting with tools and instruments such as wires, pins, screws or drills.

In particular embodiments, the surgical device may comprise one or more functional elements which are insertion elements which are reversibly connectable to the surgical device, particularly to the support structure. The insertion elements may comprise a guiding element for guiding a surgical operation, such as cutting, drilling, screwing, reshaping, reaming and implant positioning. In particular embodiments, the surgical device may comprise a first and a second insertion element, corresponding to a first surgical plan and a second (alternative) surgical plan. The different insertion elements may allow intra-operative switching between different pre-operatively planned surgical procedures.

In particular embodiments, the support structure or body of the surgical device may comprise a handle bar. In certain embodiments, the handle bar may be used by the surgeon for positioning the device and/or for keeping the guide in a stable position. In particular embodiments, this handle bar is a dedicated feature for positioning the device and/or exerting pressure onto the device during/after placement on the body part.

In particular embodiments the patient-specific surgical devices envisaged herein are further provided with a patient-specific visual aid which matches exactly with the glenoid contour of the patient. More particularly, the shape of the patient-specific visual aid is conformal with the glenoid contour of the patient. The visual aid is typically used for the evaluation of the correct unique position of the guide after placement.

Also provided herein are surgical tools for facilitating the positioning of an implant and/or guide into or onto the glenoid in the body of an animal or human patient.

In further particular embodiments of the improved patient-specific devices as envisaged herein said patient-specific device is a surgical patient-specific device. More particularly said patient-specific device is a shoulder guide.

Also provided herein are methods for the manufacture of the surgical tools described herein.

The surgical guiding tools as envisaged herein comprise patient-specific contact points and/or surfaces. The generation of patient-specific surgical tools is done based on pre-operative images of the anatomy surrounding the glenoid, and planning of the surgery. More particularly, the generation of patient-specific surgical tools is done based on preoperative images of the glenoid and planning of the surgery.

The methods for producing the surgical tools as envisaged herein typically comprise the steps of:
 a) identifying and selecting, based on volume information of the glenoid from a patient, features of the bone on or surrounding the glenoid which are suitable for fitting patient-specific positioning elements; and
 b) designing, based on the installation direction of said surgical device and the information obtained in step a), a surgical device as envisaged herein.

In particular embodiments, the methods may also comprise the steps of obtaining said relevant information for the design of the devices envisaged herein.

Accordingly, in particular embodiments, methods for producing the surgical tools according to the present invention may comprise the steps of:
 a1) obtaining volume information of the glenoid from a patient; and
 a2) obtaining the installation direction of a glenoid implant or guide for said patient;
 a3) identifying and selecting parts of the glenoid and surrounding bone which are suitable for fitting patient-specific elements; and
 b) designing and optionally producing a surgical guiding tool based on the information obtained in steps a), b) and c).

The step of obtaining volume information typically may comprise obtaining digital patient-specific image information which can be done by any suitable means known in the art, such as for example a computer tomography (CT) scanner, a magnetic resonance imaging (MRI) scanner, an ultrasound scanner, or a combination of Roentgenograms. A summary of medical imaging has been described in "Fundamentals of Medical imaging", by P. Suetens, Cambridge University Press, 2002.

The methods envisaged herein thus comprise identifying and selecting parts of the bone on and/or surrounding the glenoid which are suitable for fitting patient-specific elements. This selection step will be based on a number of criteria which may include one or more of the following

- the position of the part relative to the glenoid and the envisaged positioning of the device;
- the shape and/or surface of the part, more particularly with regard to provide a patient-specific outline based on which a specific fit can be ensured;
- the rigidity of the part;
- the accessibility of the part during surgery and more particularly for positioning a device thereon.

The methods also encompass the step of designing the device based on the suitable parts of the glenoid identified and the installation direction of the device, i.e. the surgical planning. More particularly, the step of designing will encompass determining the positioning of one or more, typically two or more positioning elements, wherein the positioning element or the combination of the two or more patient-specific positioning elements ensures a specific and secure fit of the device when positioned onto the bone. This design will typically be based on the requirement that the one or more positioning elements ensure an accurate positioning of the device (by allowing only one correct fit) and/or restrict the freedom of movement of the device after positioning correctly on the bone. In particular embodiments, as detailed above, ensuring a secure fit implies ensuring that both translational and rotational movement of the device is restricted when the fitting of the positioning elements on the bone. In particular embodiments, the positioning elements are designed such that they clamp around the outside of the glenoid rim. In particular embodiments, this can be achieved by two discrete positioning elements envisaged to interact with the exterior bone surface of the glenoid rim on opposing sides of the glenoid cavity. In particular embodiments, the design includes the provision of a hinge in one or more of the positioning elements to allow placement of the device over the rim. A further aspect of the design encompasses determining the appropriate position and orientation of the functional element, such as the guiding element on the device.

In particular embodiments, the methods envisaged herein further encompass manufacturing the device based on the design.

In a particular embodiment, Additive Manufacturing (AM) techniques are used for manufacturing the surgical guiding tools, or parts thereof. AM techniques are particularly useful to manufacture patient-specific contact surfaces, or to produce the surgical guiding tools in one piece. As an example, the manufacturing of medical-image-based patient-specific surgical instruments via AM is described in U.S. Pat. No. 5,768,134 (Swaelens et al).

AM can be defined as a group of techniques used to fabricate a tangible model of an object typically using three-dimensional (3-D) computer aided design (CAD) data of the object. Currently, a multitude of Additive Manufacturing techniques is available, including stereolithography, Selective Laser Sintering, Fused Deposition Modeling, foil-based techniques, etc.

Selective laser sintering uses a high power laser or another focused heat source to sinter or weld small particles of plastic, metal, or ceramic powders into a mass representing the 3-dimensional object to be formed.

Fused deposition modeling and related techniques make use of a temporary transition from a solid material to a liquid state, usually due to heating. The material is driven through an extrusion nozzle in a controlled way and deposited in the required place as described among others in U.S. Pat. No. 5,141,680.

Foil-based techniques fix coats to one another by means of gluing or photo polymerization or other techniques and cut the object from these coats or polymerize the object.

Typically AM techniques start from a digital representation of the 3-D object to be formed. Generally, the digital representation is sliced into a series of cross-sectional layers which can be overlaid to form the object as a whole. The AM apparatus uses this data for building the object on a layer-by-layer basis. The cross-sectional data representing the layer data of the 3-D object may be generated using a computer system and computer aided design and manufacturing (CAD/CAM) software.

The surgical guiding tools envisaged herein may be manufactured in different materials. Typically, only materials that are biocompatible (e.g. USP class VI compatible) with the animal or human body are taken into account. Preferably the surgical guiding tool is formed from a heat-tolerable material allowing it to tolerate high-temperature sterilization. In the case selective laser sintering is used as an AM technique, the surgical template may be fabricated from a polyamide such as PA 2200 as supplied by EOS, Munich, Germany or any other material known by those skilled in the art may also be used.

While the above disclosure provides reference to particular embodiments, it will be understood by those skilled in the art that various changes or modifications in form and detail may be made without departing from the scope and spirit of this concepts described herein.

Further illustration is provided particular embodiments described below.

EXAMPLES

Example 1

Figure 1:
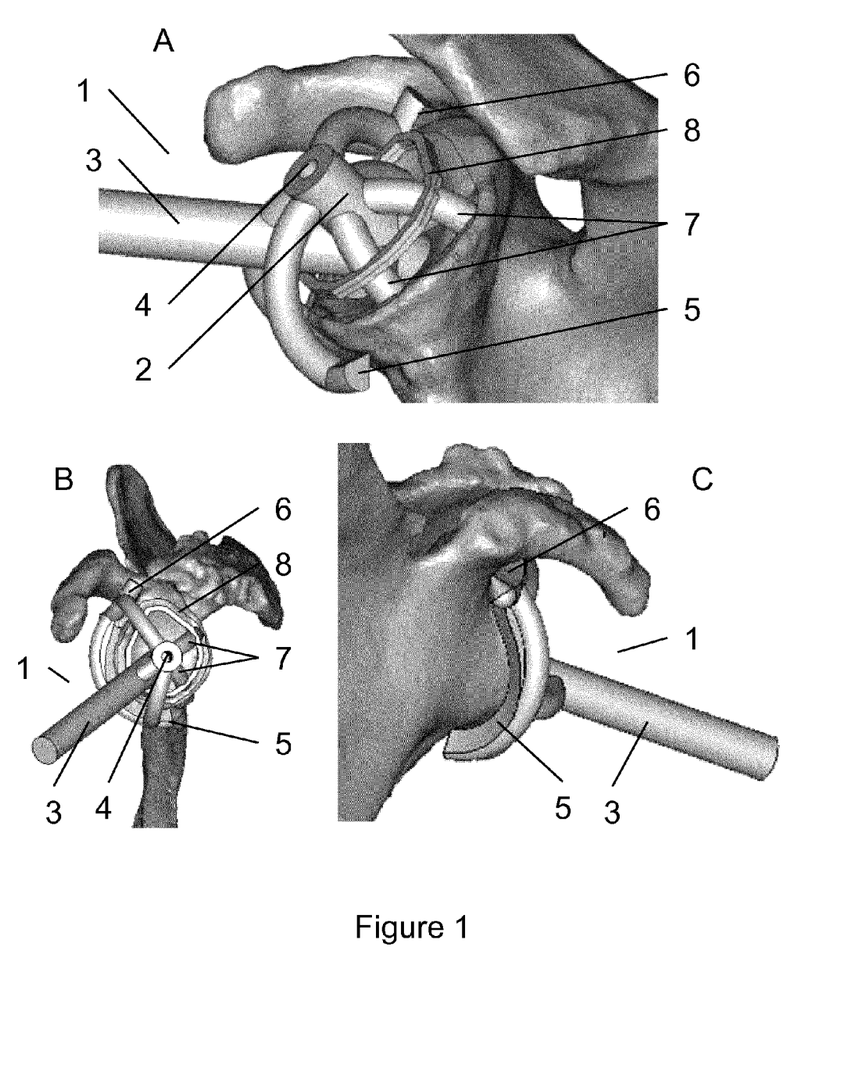
FIG. 1: Illustration of an embodiment of a patient-specific surgical guide positioned on the glenoid.

Surgical Pin Guiding Instrument for Total Shoulder Arthroplasty (TSA) with Deltopectoral (DP) Approach and for Reverse Shoulder Arthroplasty (RSA) with Superiolateral (SP) Approach The present example relates to a patient-specific instrument for shoulder surgery. According to a particular embodiment envisaged, the surgeon selects a patient for shoulder replacement and takes a scan of the patient's anatomy, for example using magnetic resonance imaging (MRI) or computed tomography (CT). Based on this scan a three dimensional model of the patient's anatomy is made. Then, pre-operative plannings for two or more shoulder procedures (for example TSA or RSA) are reviewed. The surgeon approves the pre-operative plans but does not need to select a procedure. A patient-specific surgical guiding instrument (1) is then developed based on the approved plans of the surgeon. The device may comprise a support structure (2), a handle bar (3), a drill cylinder (4), several patient-specific elements including an anterior glenoid neck support (5), an inferior coracoid base support (6) and support at the anterior and posterior glenoid surface and/or rim (7), and optionally a floating contour above the glenoid surface conform the glenoid rim geometry (8) as shown in FIGS. 1A, B and C. The support structure (2) is a general structure connecting the different parts of the surgical guiding instrument (1). The handlebar (3) is used by the surgeon for keeping the guide in stable position. The handlebar (3) is directed mostly in the transverse plane with a 45° angulation relative to scapular wing plane and the sagittal plane. The drill cylinder (4) preferably rests on the glenoid surface for rigidity during drilling. The patient-specific guiding elements further comprise several patient-specific elements including an anterior glenoid neck support (5) (shown with knife contact) to prevent translational movement, an inferior coracoid base support (6) (shown with knife contact) to prevent rotational movement in the sagittal plane and one or more supports at the anterior and/or posterior glenoid surface and/or rim (7) to prevent rotational movement in transverse plane and correction of retroversion in B2 or C glenoid deformity. Optionally a floating contour (8) above the glenoid surface is provided. The contour matches patient-specifically with the glenoid rim geometry and enables a visual check of the position. Different insertion elements which are connectable to the support structure may be provided, each may comprise a guiding feature corresponding with one of the two or more pre-operative plans. Due to the different insertion elements, the guiding instrument allows intra-operative switching between different pre-operatively planned surgical procedures.

Example 2

Surgical Pin Guiding

Figure 2:
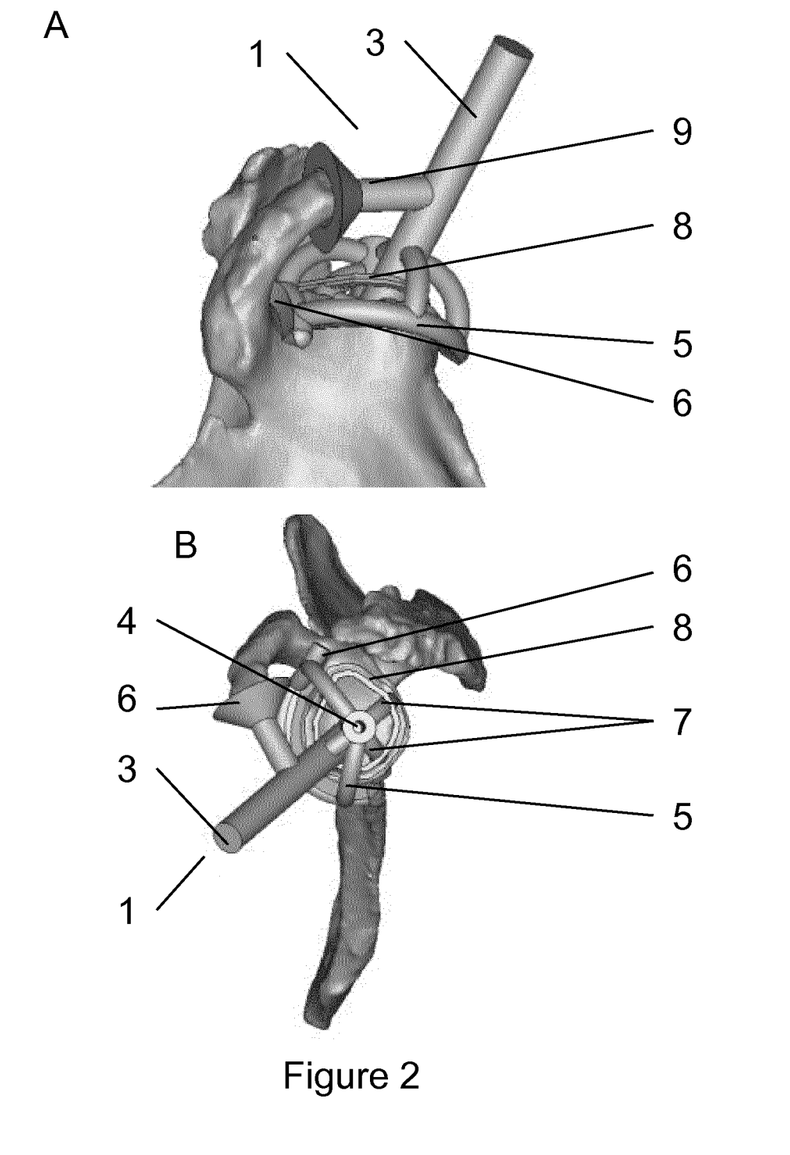
FIG. 2: Illustration of an embodiment of a patient-specific surgical guide positioned on the glenoid comprising an additional patient-specific element that provides a support at the coracoid tip.

The present example relates to a patient-specific instrument according to a particular embodiment as envisaged herein for shoulder surgery similar to the one described in example 1 and as shown in FIGS. 2A and B. The device may further comprise an additional patient-specific element that provides a support at the coracoid tip (9). Typically, the cone synapse provides a 0.7 mm contact offset (leaving the possibility to leave soft tissue layers) for good rotational position in frontal plane. This additional patient-specific element can further be aided by supports on the superior and/or inferior glenoid surface. While this patient-specific element would not provide the accuracy that is provided with the other patient-specific elements described, the support at the coracoid tip (9) does provide a faster and easier positioning providing a feelable fit on the glenoid tip.

Example 3

Surgical Pin Guiding Instrument

The present example relates to a patient-specific instrument according to a particular embodiment envisaged herein for shoulder surgery similar to the one described in example 1 and 2 and as shown in FIGS. 3, 4, 5 and 6.

Figure 3:
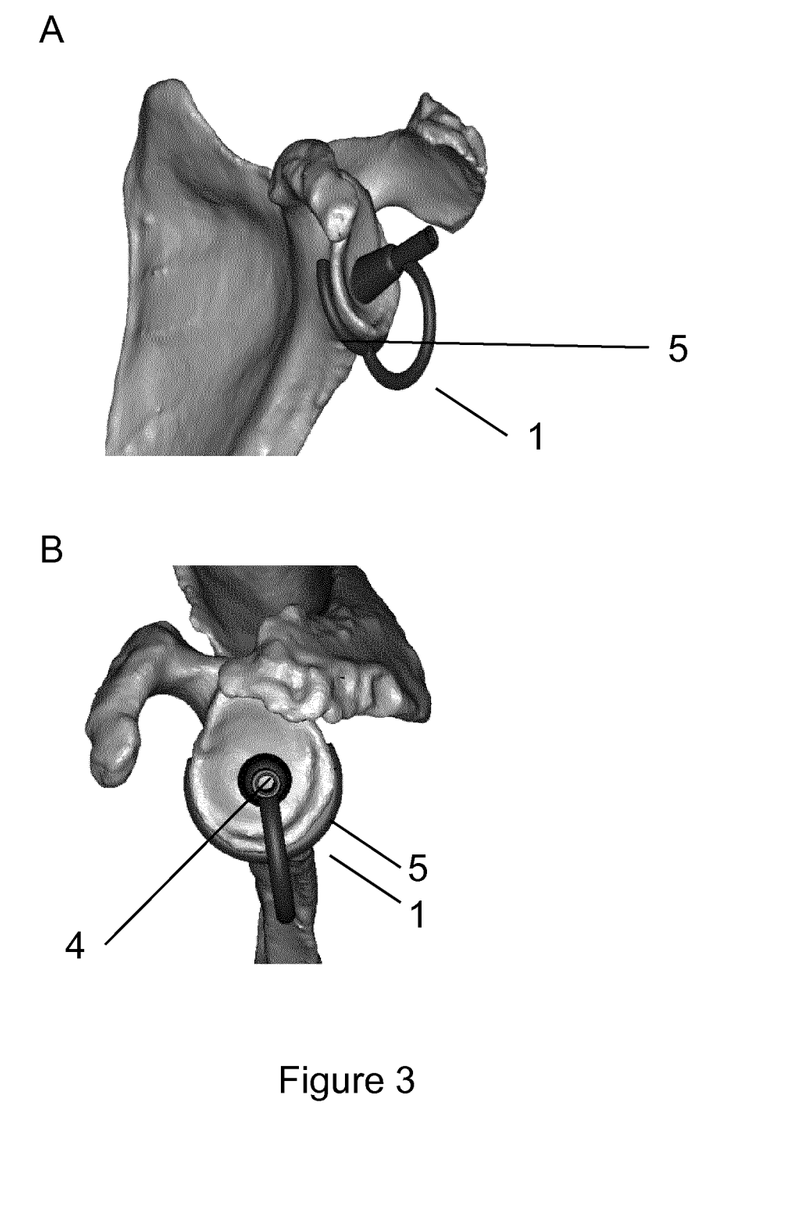
FIG. 3: Illustration of an embodiment of a patient-specific surgical guide positioned on the glenoid with ring support at the anterior glenoid neck.

FIG. 3 provides a patient-specific instrument according to a particular embodiment envisaged herein wherein the device may comprise a patient-specific element that provides an anterior glenoid neck support (5) (shown with knife contact) to prevent translational movement. The anterior glenoid neck support (5) is a ring which fits around the rim of the glenoid.

Figure 4:
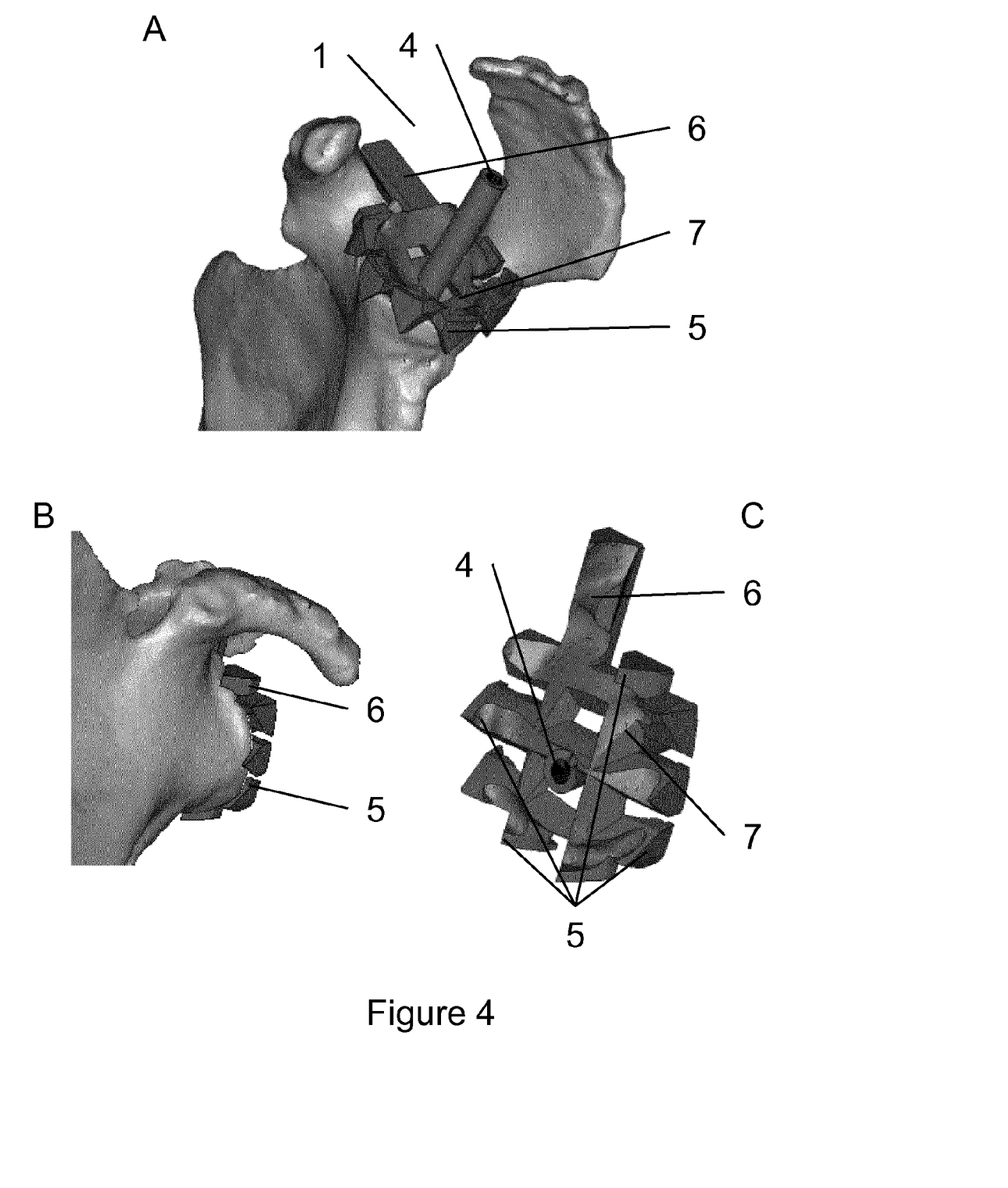
FIG. 4: Illustration of an embodiment of a lattice structured patient-specific surgical guide positioned on the glenoid.

FIG. 4 provides a patient-specific instrument according to a particular embodiment envisaged herein wherein the device may comprise a multitude of patient-specific elements providing support on the anterior glenoid neck (5) (shown a several discrete contacts), on the inferior coracoid base support (6) (shown as a discrete contact) and one or more supports at the anterior and/or posterior glenoid surface and/or rim (7). Such a lattice structured patient-specific instrument was seen to provide an exceptional good accuracy and stability.

Figure 5:
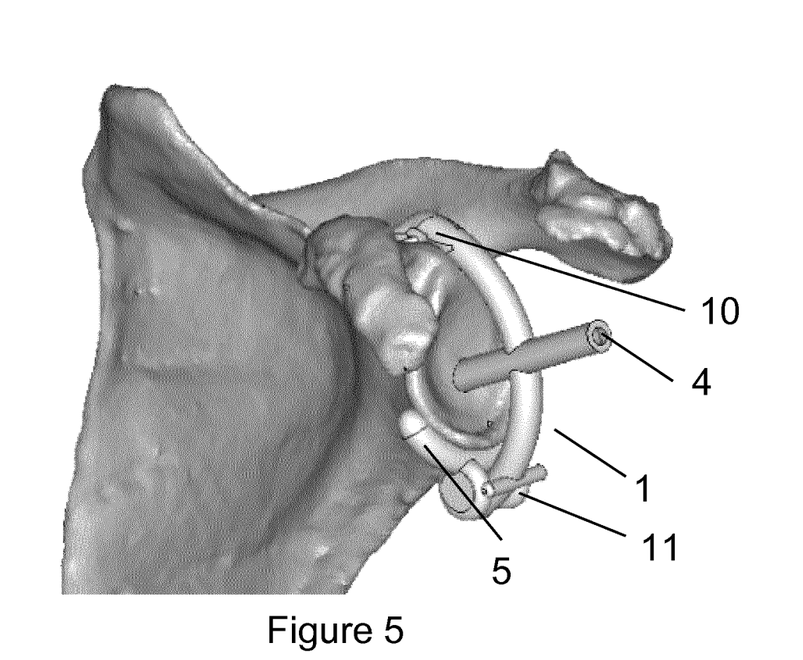
FIG. 5: Illustration of an embodiment of a patient-specific surgical guide positioned on the glenoid comprising a catapult mechanism.

FIG. 5 provides a patient-specific instrument according to a particular embodiment envisaged herein wherein the device may further comprise a catapult mechanism comprising a locking feature (10) and a hinge feature (11) which allows locking the guide once it has been placed in the correct position. This catapult mechanism can for instance be a handle mechanism that clicks into the remainder of the guide and thereby rotates the lower part or for instance a spring element, automatically delivering clamping force once put into the correct location.

Figure 6:
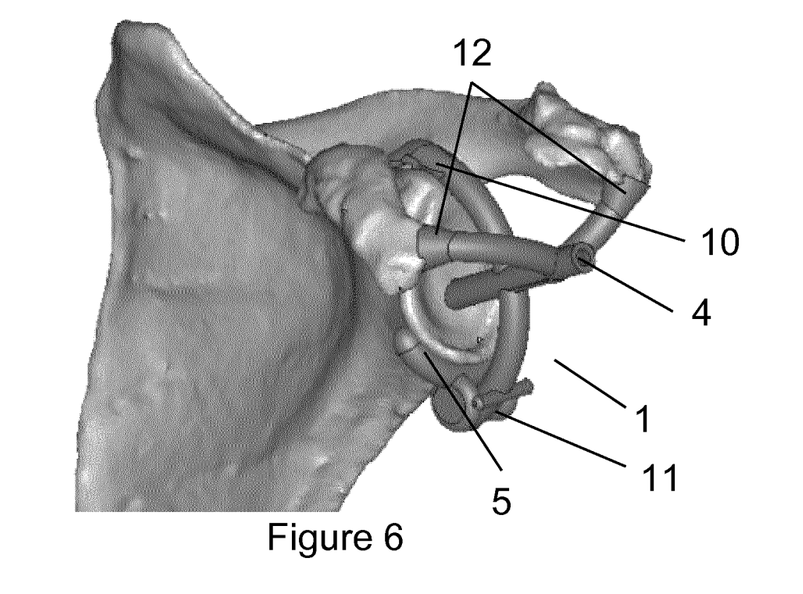
FIG. 6: Illustration of an embodiment of a patient-specific surgical guide positioned on the glenoid comprising a catapult mechanism and provided with additional synapses.

FIG. 6 provides a patient-specific instrument according to a particular embodiment envisaged herein similar to the one described in FIG. 5, but with additional synapses (12) to increase stability by extending to distant bony and/or soft tissue landmarks on the processus coracoideus (coracoid process) and acromion.

Example 4

Hinge Clamp

Figure 7:
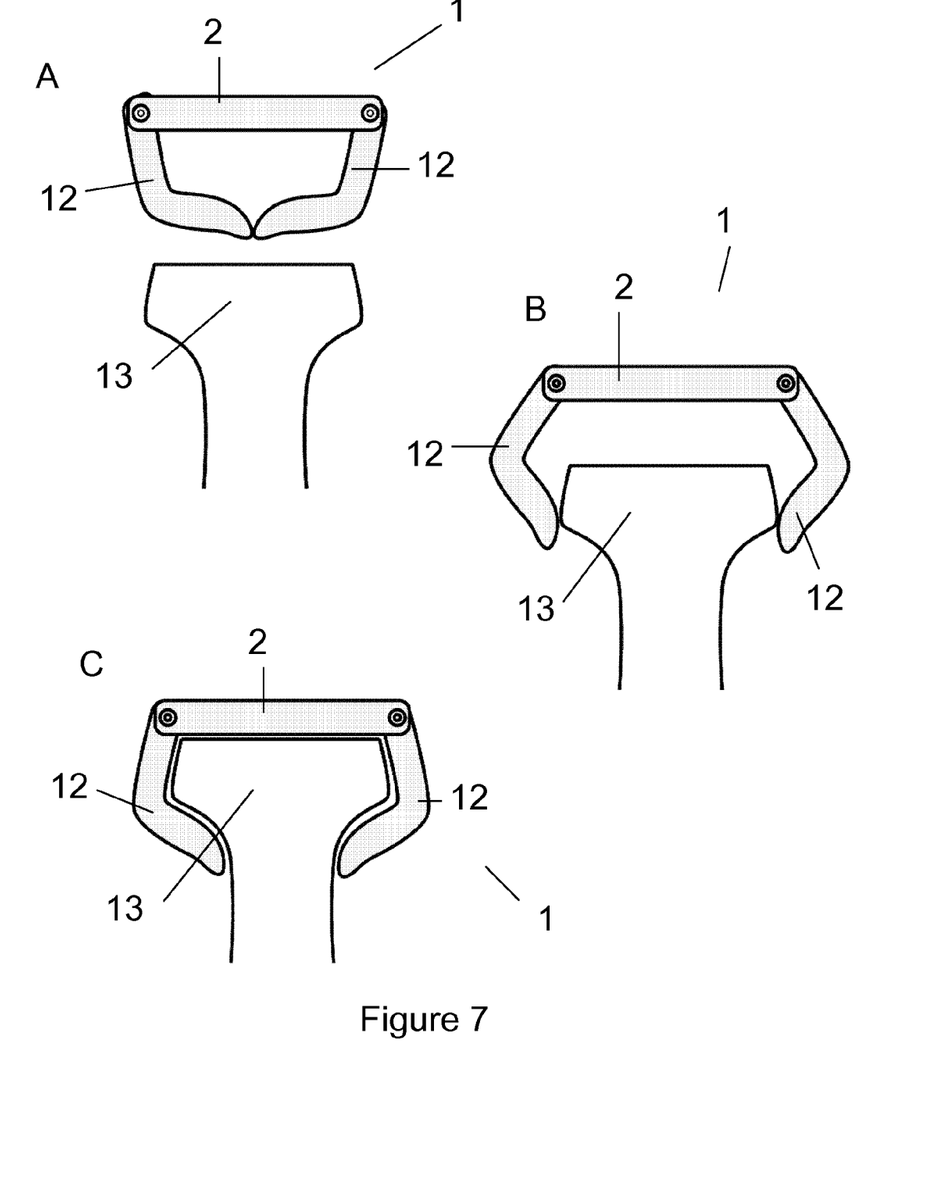
FIG. 7: Illustration of an embodiment of a patient-specific surgical guide positioned on the glenoid comprising a hinge clamp.

FIG. 7 A-C further provides a patient-specific guiding instrument (1) according to a particular embodiment envisaged herein. According to this embodiment, the guide body is provided with several positioning elements (12) which clamp over shoulder bone (13). The positioning features comprise a hinge. This allows the positioning feature to take different positions for placement and for securing onto the shoulder bone. The positioning feature can be adjusted to the anatomy of the bone so as to ensure a tight fit of the surgical instrument over the bone, as shown in FIG. 7C.

What is claimed is:

1. A patient-specific surgical guide for positioning onto a glenoid of a patient, comprising: a support structure; a guiding element; and at least two patient-specific positioning elements linked to or forming an integral part of the support structure, each comprising a patient-specific surface which conforms with at least part of at least one feature of the bone on or around the glenoid, at least one of the patient-specific surfaces conforming with a part of the bone other than the glenoid and wherein a combination of the two or more patient-specific positioning elements ensures a restriction of movement of the patient-specific surgical guide in both translational and rotational directions when positioned onto the bone.

2. The patient-specific surgical guide of claim 1, wherein the at least one feature of the bone on or around the glenoid include at least one of a glenoid neck, a coracoid process, a glenoid surface, and a glenoid rim.

3. The patient-specific surgical guide of claim 1, wherein the support structure includes a patient-specific surface which conforms with at least part of the glenoid surface and at least part of the glenoid rim.

4. The patient-specific surgical guide of claim 1, wherein the at least two patient-specific positioning elements comprise three patient-specific positioning elements, and wherein the three patient-specific positioning elements include an anterior glenoid neck support, an inferior coracoid base support, and a support at the anterior and posterior of at least one of the glenoid surfaces and glenoid rims.

5. The patient-specific surgical guide of claim 1, further comprising a visual aid matching a contour of the glenoid.

6. The patient-specific surgical guide of claim 1, further comprising at least one dedicated functional feature, wherein the at least one dedicated functional feature includes at least one of a wire, a pin, a screw, and a drill.

7. The patient-specific surgical guide of claim 1, wherein the guiding element comprises a drill cylinder.

8. The patient-specific surgical guide of claim 1, wherein the support structure comprises a handle bar.

9. The patient-specific surgical guide of claim 8, wherein said handle bar is configured for exerting pressure onto the patient-specific surgical guide during positioning of the patient-specific surgical guide onto the glenoid.

10. The patient-specific surgical guide of claim 8, wherein said handle bar is configured for exerting pressure onto the patient-specific surgical guide when positioned onto the glenoid.

11. The patient-specific surgical guide of claim 8, wherein said handle bar is configured for maintaining a position of the patient-specific surgical guide when positioned onto the glenoid.

12. The patient-specific surgical guide of claim 1, wherein the at least two patient-specific positioning elements are reversibly connected to the support structure.

* * * * *